United States Patent
Hwang et al.

[19]

[11] Patent Number: 5,961,911
[45] Date of Patent: Oct. 5, 1999

[54] PROCESS FOR MANUFACTURE OF CLOSURE ASSEMBLY

[75] Inventors: Chorng-Fure Robin Hwang, Cary; Frank E. Martin, Durham; Tim M. Sullivan; Joel L. Williams, both of Cary, all of N.C.

[73] Assignee: Becton Dickinson and Company, Franklin Lakes, N.J.

[21] Appl. No.: 08/985,955

[22] Filed: Dec. 5, 1997

[51] Int. Cl.⁶ .................................................. B29C 45/14
[52] U.S. Cl. ................................. 264/268; 264/319
[58] Field of Search ..................... 264/268, 135, 264/319, 331.13, 331.15, 267; 425/809

[56] References Cited

U.S. PATENT DOCUMENTS

| | | | |
|---|---|---|---|
| 3,689,625 | 9/1972 | Zipper | 264/268 |
| 4,196,162 | 4/1980 | Stichter | 264/131 |
| 4,274,822 | 6/1981 | Tamai et al. | 425/127 |
| 4,312,824 | 1/1982 | Mori et al. | 264/268 |
| 4,314,799 | 2/1982 | Amberg et al. | |
| 4,398,875 | 8/1983 | Kawashima et al. | 425/127 |
| 4,497,765 | 2/1985 | Wilde et al. | 264/266 |
| 4,588,465 | 5/1986 | Paciorek | 156/220 |
| 4,798,122 | 1/1989 | Gisler et al. | 264/250 |
| 5,447,674 | 9/1995 | Schellenbach | 264/255 |
| 5,650,113 | 7/1997 | Gregory et al. | 264/268 |
| 5,658,518 | 8/1997 | Ingram | 264/268 |
| 5,686,040 | 11/1997 | Taber | 264/268 |

FOREIGN PATENT DOCUMENTS 0 702 032 A2  3/1996  European Pat. Off. .

*Primary Examiner*—Angela Ortiz
*Attorney, Agent, or Firm*—Richard E. Brown

[57] ABSTRACT

A process for making a closure assembly includes placing a closure cap portion in a compression mold, introducing a melt of elastomer, pressing the melt into a septum against the cap and applying a foil barrier against the septum. The process may be performed in a rotary compression molding apparatus.

10 Claims, 2 Drawing Sheets ice# PROCESS FOR MANUFACTURE OF CLOSURE ASSEMBLY

FIELD OF THE INVENTION

This invention relates to molding processes, and more particularly relates to an improved process by which multi-component closures may be molded by an operationally simple and cost efficient process.

BACKGROUND OF THE INVENTION

Multi-component closures for vessels such as flasks, vials, tubes and the like have conventionally been manufactured by injection or compression molding of the individual components and subsequently combining the individual parts in one or more separate processes. For example, in the manufacture of tube closures, a septum for penetration by a needle is stamped out of an elastomeric sheet and adhered to a preformed cap portion. Additional components, such as a foil lining, may then be added.

Such processes are inefficient from a processing standpoint and also result in material waste at each step. In all injection molding machines, some polymer remains in the sprue after the mold is closed, leaving a projecting piece or tab which must be removed after the product is ejected from the mold. Often, the tabs are simply discarded, or for reasons of economy, may be recovered and recycled. In either case the inefficiency and additional cost which result lead to reduced productivity from the mold.

In compression molding, an apparatus which resembles a waffle iron is used wherein melted polymer fills all mold cavities without passing through gates and runners. When all the cavities are filled, the mold is closed and heat and pressure are applied from a hydraulic press. While this process eliminates gates and runners, a surplus of polymer must be used to ensure total cavity fill. The heat and pressure cause the polymer to fill the cavity and cause spillage out into overflow grooves. Polymer in the grooves, like the tabs in injection molding, must be recycled or discarded. Compression molding, like injection molding, is inherently a batch process but is less efficient than injection molding, because a separate machine is required to separate the individual articles from the single large "waffle" which comes out of the compression mold.

Rotary compression molding is a recent development in which individual molds on the track of a continuously revolving platform are individually charged with a melt of thermoplastic material. Compression and heating of the thermoplastic in the mold by a plunger forms the desired article. The mold-plunger unit advances along the track and is opened when the article has solidified.

SUMMARY OF THE INVENTION

In a process for making a closure assembly, a closure cap having an open lower end and a top wall having an opening is placed, top wall down, in a compression mold. A predetermined quantity of a thermoplastic elastomer (TPE) is added to the cap and pressed by a matching male forming pin into a septum which covers the opening and adheres to the underside of the top wall. A permeability lowering barrier may then be pressed against the septum. In a preferred process, the cap is introduced to the female cavity of a compression mold at a first station of a rotary compression molding apparatus and subsequent steps of the process are performed sequentially at later stations.

Conventional processes for making closure assemblies include preparing a performed sheet of elastomeric material, laminating a foil barrier material thereto, stamping septum-foil units from the laminated sheet and adhering these to injection molded caps, often with an adhesive. These procedures are time consuming and up to 30% of the elastomer is lost during the stamping operation and must be discarded or recycled. The present invention overcomes the lost time and material of conventional processes, eliminates any need for adhesive, and is accordingly much more efficient.

DETAILED DESCRIPTION

While this invention is satisfied by embodiments in many different forms, there will herein be described in detail embodiments of the invention with the understanding that the present disclosure is to be considered as exemplary of the principles of the invention and is not intended to limit the invention to the embodiments illustrated and described. The scope of the invention will be measured by the appended claims and their equivalents.

In the process of the invention, a multi-component closure assembly is produced by compression molding a puncturable septum directly across an opening in a cap portion, and then, without removing the cap-septum unit from the mold, a permeability-lowering barrier is introduced and adhered to the septum.

Figure 1:
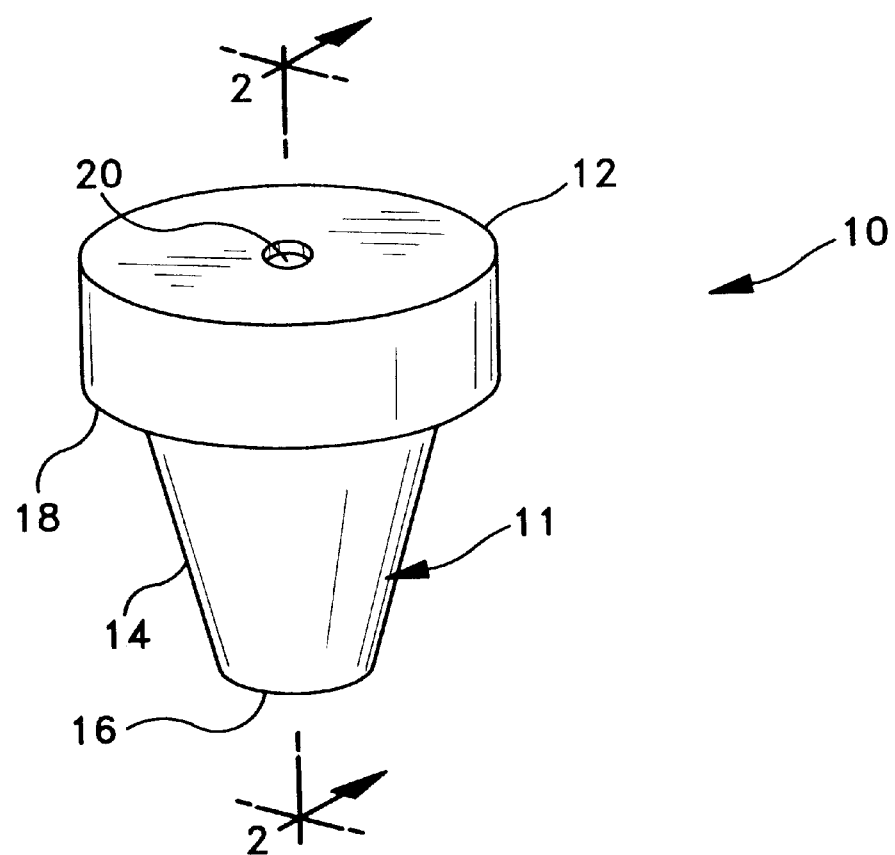
FIG. 1 is a perspective view of a closure assembly made by the process of the invention.
Figure 2:
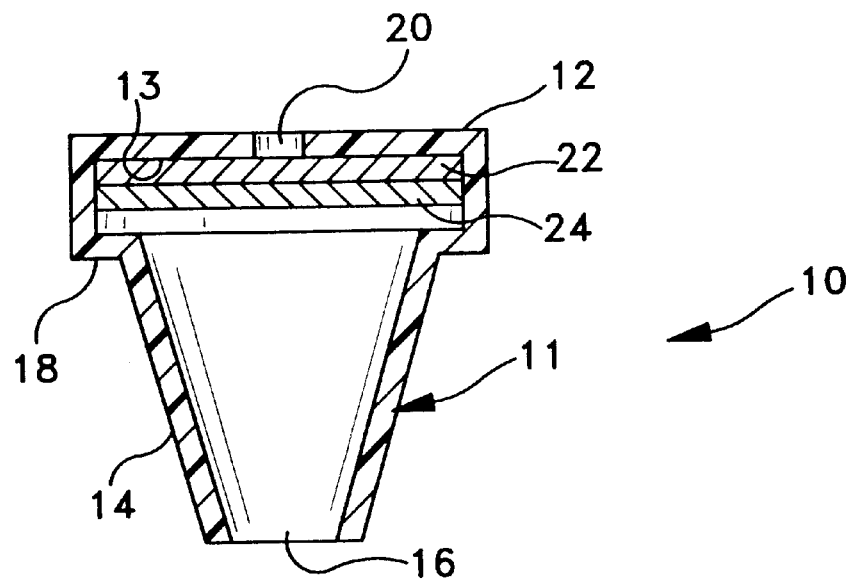
FIG. 2 is a vertical sectional view of the assembly of FIG. 1 taken along the line 2—2 thereof.
Figure 3:
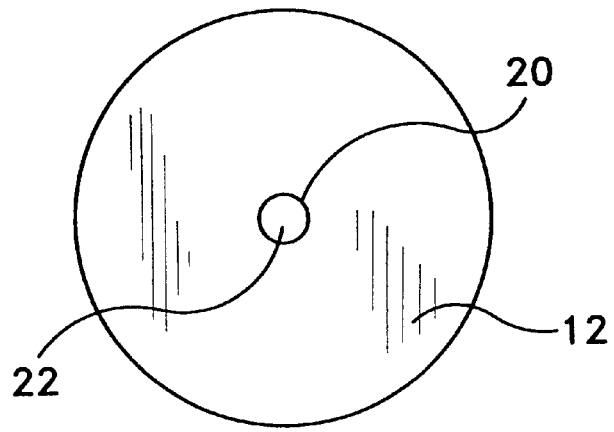
FIG. 3 is a top plan view of the assembly of FIG. 1.

Adverting now to the drawings, FIGS. 1–3 illustrate a typical tube closure assembly fabricated by the process of the invention. Assembly 10 includes a cap portion 11 having an annular top wall 12 having a bottom edge 13 and a side wall 14 defining an open bottom end 16. Side wall 14 may include a shelf 18 for engagement with the lip of a tube (not shown). Top wall 12 includes an opening 20 to receive a needle. A septum 22 is adjacent and adhered to bottom edge 13 of cap portion 11. A permeability lowering barrier 24 is adjacent and adhered to septum 22. As shown in FIG. 3, septum 22 is visible through opening 20 when the closure assembly is viewed from above.

The cap portion 11 of the assembly may be fabricated by any conventional process, such as injection molding, and may be of any conventional plastic which is compatible with and forms a secure bond with the material selected for the septum, as delineated below. Preferred plastics for the cap are polyolefins, such as polyethylene or polypropylene, polyethylene terephathalate (PET) and polystyrene. Fabrication of the cap portion is not part of this invention. The injection molded cap portion may be placed in the female cavity of a compression mold with top wall 12 in the bottom of the cavity so that open bottom end 16 faces up. A quantity of melt of TPE predetermined to form septum 22 is then introduced, preferably by extrusion, into the cap portion in the mold cavity. A matching male forming pin is introduced into the female cavity to force the elastomer into the shape of septum 22 which is thereby pressed against and bonds with bottom edge 13 of cap top wall 12.

Any TPE which forms a secure bond to the cap may be used for the septum. Suitable thermoplastics for septums to be used with polystyrene caps are for example acrylonitrile-butadiene-styrene or styrene-butadiene rubbers. For PET caps a septum of polyester TPE, such as HYTREL™ (DuPont) is preferred.

Elastomers suitable for septums to be used with polyolefin caps are thermoplastic polyolefin rubbers, generally referred to as TPOs, for example ethylene-propylene-diene monomer (EPDM) rubber in a polypropylene matrix, commercially available under the trade name SANTOPRENE™ from AES (Advanced Elastomer Systems, Akron, Ohio).

A preferred elastomer for septums to be used with polyolefin caps is the class of copolymers known in the art as metallocene copolyolefins, i.e., copolymers made using metallocene catalysts. Exemplary of such products are copolymers of ethylene with an alpha olefin of 3–20 carbon atoms. These products are commercially available from Exxon under the trade name EXACT™ or from Dow under the trade name ENGAGE™.

The most preferred elastomer for a septum to be used with a polyolefin cap is a metallocene copolymer of the EXACT or ENGAGE series which has been silane-grafted to contain about 0.2–10% by weight of silane. Silane-grafted metallocene polyolefin copolymers are well known in the art and are fully described in European Patent Application EP 0 702 032A2 and International Application No. WO 95/29197. They form exceptionally strong bonds to polyolefin caps. Silanes which may be grafted to polyolefins are sold by HULS AG (Somerset, N.J.) under the trade name DYNA-SYLAN™. A preferred grafting agent is vinyl trimethoxy silane.

If it is desired that the septum be hardened, the capseptum unit in the mold may optionally be exposed to moisture to crosslink the polymer of the septum through siloxane groups. Crosslinking of silane-grafted metallocene polyolefins is conventional in the art.

Without removing the cap-septum unit from the mold, a permeability lowering barrier may be pressed against and bonded to the septum. The barrier preferably is of foil, most preferably aluminum foil, though any other suitable material as known in the art may be used. If a more secure bond between the septum and the foil barrier is desired, the foil may be coated with any suitable adhesive such as CHEM-LOK™ (Lord Corporation, Erie, Pa.). The barrier may be about 0.3 to 3 micron thick.

The preferred process of the invention is continuous. In this embodiment of the invention, a line of female compression molds moves along a track. Each mold visits sequentially a series of stations where an operation in the process takes place. Thus, at a first station along the track, the mold receives the injection molded cap portion, as described above. The mold containing the cap advances along the track to a second station where the predetermined quantity of elastomer is extruded into the cap in the mold. At this station, the mating male forming pin may be introduced to compression mold the elastomer into the shape of the septum, or preferably, the mold, after receiving the elastomer, may be advanced to the next sequential station where the forming pin enters the mold and compression molds the elastomer into the septum and against the bottom edge of the top wall of the cap. The forming pin may then be retracted and the foil or foil-adhesive unit introduced and pressed against the septum by reentry of the forming pin.

Alternatively, the mold containing the cap-septum unit may be further advanced and the foil barrier introduced at a subsequent station. An apparatus suitable for the continuous process of the invention is described in detail in U.S. Pat. No. 4,314,799.

In any closure, it is critical that the septum bond securely to the cap so that no separation or leakage occurs. For example, it is readily seen that failure of the septum-cap seal would compromise the vacuum in an evacuated blood collection tube and lead to incomplete sample collection. In the present invention, it has been found that compression molding the melt bonds the elastomeric septum against the cap with sufficient strength so that adhesive is not required and leakage does not occur. Bond strength between septum and cap in closures made by the process of the invention and the prior art may be tested qualitatively for leakage by the procedure of the Example.

EXAMPLE

The closure to be tested for leakage was inserted into the open end of a 16×100 mm plastic tube. Ten ml of water were added (80% fill), and the tube was dropped from heights of 78 and 39 in. onto a laboratory floor (simulated hospital floor). The tubes were then visually examined for leakage through the cap-septum seal. No separation of septum from cap was observed with the following closure assemblies made by the process of the invention, and no leakage was observed.

1) polystyrene cap—HYTREL septum-foil barrier
2) polypropylene cap—SANTOPRENE septum-foil barrier
3) polypropylene cap—silane-grafted EXACT septum-foil barrier

What is claimed is:

1. A process for making a closure assembly comprising:
   a) placing a plastic cap portion of a closure assembly having a top wall defining an opening into the female cavity of a compression mold, said cap portion being placed with said top wall adjacent to the bottom wall of said mold;
   b) adding a thermoplastic elastomer to said cap portion;
   c) pressing said elastomer into a septum sealed against said top wall and covering said opening; and
   d) affixing a permeability lowering barrier to said septum, said assembly being puncturable through said opening and said septum.

2. The process of claim 1 wherein said elastomer is pressed into said septum by a matching male forming pin.

3. The process of claim 2 wherein said cap portion is placed in the female cavity of a compression mold at a first station of a rotary compression molding apparatus.

4. The process of claim 1 wherein said plastic cap is of polystyrene, polyolefin or polyethylene terephthalate.

5. The process of claim 1 wherein said elastomer is selected from a group consisting of styrene-butadiene rubber, ethylene propylene diene monomer rubber, a copolymer of ethylene and an alpha olefin of 3–20 carbon atoms, and a silane grafted copolymer of ethylene and an alpha olefin of 3–20 carbon atoms.

6. A process for making a closure assembly comprising:
   a) placing a polyolefin cap portion of a closure assembly having a top wall defining an opening into the female cavity of a compression mold, said top wall being adjacent to the bottom wall of said mold;
   b) introducing a melt of a copolymer of ethylene and an alpha olefin of 3–20 carbon atoms into said cap portion;
   c) pressing said copolymer with a matching male pin to form a septum against said top wall and covering said opening; and
   d) affixing a permeability-lowering barrier to said septum, said assembly being puncturable through said opening and said septum.

7. The process of claim 6 wherein said copolymer includes silane grafts.

8. The process of claim 7 further comprising crosslinking said septum of silane-grafted copolymer.

9. A process for making a tube closure assembly comprising:

a) placing a polyolefin cap portion of a closure assembly having a top wall defining an opening into the female cavity of a compression mold at a first station of a rotary compression molding apparatus, the top wall of said cap portion being placed adjacent to the bottom of said mold;

b) adding a predetermined quantity of a melt of a silane-grafted copolymer of ethylene and an alpha olefin of 3–20 carbon atoms into said cap portion in said female cavity;

c) pressing said copolymer with a matching male pin to form a septum against said top wall and covering said opening; and d) pressing a permeability-lowering barrier against said septum with said male pin, said assembly being puncturable through said opening and said septum.

10. The process of claim 9 wherein the septum is crosslinked.

* * * * *